(12) United States Patent
Hemmati-Brivanlou et al.

(10) Patent No.: US 6,337,392 B1
(45) Date of Patent: Jan. 8, 2002

(54) LENS TRANSCRIPTIONAL CONTROL ELEMENTS AND METHODS OF USE THEREOF

(75) Inventors: Ali Hemmati-Brivanlou; Curtis R. Altmann; Sonya Williams, all of New York; Robert L. Chow, Forest Hills; Richard A. Lang, New York, all of NY (US)

(73) Assignees: The Rockefeller University; New York University, both of New York, NY (US)

( * ) Notice: Subject to any disclaimer, the term of this patent is extended or adjusted under 35 U.S.C. 154(b) by 0 days.

(21) Appl. No.: 09/306,042

(22) Filed: May 6, 1999

Related U.S. Application Data
(60) Provisional application No. 60/084,588, filed on May 7, 1998.

(51) Int. Cl.$^7$ .................. C07H 21/04; C07H 21/02; C12Q 1/68; C12P 21/04; C12N 15/00

(52) U.S. Cl. .................. 536/24.1; 536/24.31; 536/23.1; 435/6; 435/70.1; 435/320.1; 435/325

(58) Field of Search ................ 536/23.1, 24.1, 536/24.31; 435/320.1, 325, 6, 70.1

(56) References Cited

FOREIGN PATENT DOCUMENTS

| WO | WO 98 48829 | 11/1998 |
|---|---|---|
| WO | WO 99 31260 | 6/1999 |

OTHER PUBLICATIONS

Lewin; Genes IV, 1990, Building the Transcription Complex: 551–554.*
Huang et. al.; Derepression of human embryonic globin promoter by a locus–control region sequence, 1998, Proc. Natl. Acad. Sci. vol. 95:14669–14674.*
Tang et al., J. Biol. Chem., vol. 273, 7210–7221 (1998).
Pignoni et al., Cell, vol. 91, 881–891 (1997).
Chen et al., Cell, vol. 91, 893–903 (1997).
Callaerts et al., Ann. Rev. Neuroscience, 20:483–532 (1997).
Oliver et al., Mech. of Development 60, 233–239 (1996).
Mathers et al., Nature, vol. 387, 603–607 (1997).
Macdonald et al., Development 121, 3267–3278 (1995).
Cuny et al., J. Embryol. exp. Morph. 96, 151–170 (1986).
Jena et al., Experimental Cell Research, 230, 28–37 (1997).
Adams MD et al., 1997, EMBL Accession No. B65604 and Genebank Accession No. G2639042.
Altmann et al., 1997, Dev Biol, 185:119–23.
Cvekl A et al., 1996, Bioessays 8:621–630.
Duncan et al., 1998, Molicular and Cellular Biology 18:5579–86.
Fujiwara et al., 1994, Differentiation, 57:31–8.
Gehring et al., 1996, Genes to Cells, 1:11–5.
Glardon et al., 1997, Development, 124:817–25.
Grindley et al., 1995, Development, 121:1433–22.
Halder et al., 1995, Science, 267:1788–92.
Hammer RE et al., 1990, Cell 63:1099–1112.
Hanson et al., 1994, Nature Genetics, 6:168–73.
Hill et al., 1991, Nature, 354:522–5.
Kammandel et al., 1999, Developmental Biology 205:79–97.
Jordan et al., 1992, Nat Genet, 1:328–32.
Jupin I and Chua NH., 1996, EMBO J 15: 5679–89.
Lewin B, 1990, Chapter 23, pp. 451–465, Genes IV. Oxford University Press.
Li et al., 1997, Development, 124:603–15.
Li et al., 1994, Dev Biol, 162:181–94.
Mullins JJ et al., 1993, Hypertension 22:630–33.
Overbeek PA et al., 1985, Proc. Natl. Acad. Sci. USA 82:7815–19.
Plaza S et al., 1993, Cell Growth and Differentiation 4(12):1041–1050.
Plaza S et al., 1995, (a) Oncogene 10:329–40.
Plaza S et al., 1995, Mol. Cell. Biol. 15:3344–3353.
Promega Catalogue, 1996, p. 12.28–29.
Quinn et al., 1996, Genes & Development 10:435–446.
Quiring et al., 1994, Science, 365:785–9.
Seidel GE., 1993, J. Anim. Sci. 71(Suppl. 3):26–33.
Song et al., 1996, 122:627–35.
Tomarev et al., 1997, Proc Natl Acad Sci, 94:2421–6.
Van Heyningen V. and Little P.F. Cytogenet., 1995, Cell. Genet. 69:128–58.
Walther et al., 1991, Development, 113:1435–49.
Williams et al., 1998, Mechanisms of Development 73:225–229.
Xu P-X et al., 1999, Development 126:383–95.

* cited by examiner

Primary Examiner—Deborah J. R. Clark
Assistant Examiner—Peter Paras, Jr.
(74) Attorney, Agent, or Firm—Darby & Darby

(57) ABSTRACT

The present invention discloses nucleic acids containing transcriptional control elements that are lens transcriptional control elements. One such lens transcriptional control element is exemplified by the control element of the Pax-6 gene. Methods of using these lens transcriptional control elements for drug assays, diagnostics and for identifying transcription factors involved in lens development are also disclosed.

15 Claims, 3 Drawing Sheets

Figure 1

| Gene/construct name | Gene/construct map | Expression pattern | | | | | | |
|---|---|---|---|---|---|---|---|---|
| | | lens | corneal epithelium | viscera | retina | neural tube | nasal placodes |
| Pax-6 | CE —NotI— P0 Ex0 1 2 | + | + | + | + | + | + |
| P6-5.0 | CE —NotI— Ex0 lacZ SV40 t | + | + | + | + | + | − |
| P6-3.9 | CE — Ex0 lacZ SV40 t | + | + | +/− | − | − | − |
| P6-3.9-3.5 | CE — hsp68 Pr lacZ SV40 t | + | + | − | − | − | − |
| P6-2.7 | —NsiI— Ex0 lacZ SV40 t | − | − | − | − | − | − |

Figure 2

SEQUENCE LISTING

<160> NUMBER OF SEQ ID NOS: 6

<210> SEQ ID NO 1
<211> LENGTH: 526
<212> TYPE: DNA
<213> ORGANISM: Mouse

<400> SEQUENCE: 1

```
ggttacacca gaagcacccc aacctcattc ttttcacctc ctgtttaaat tactaagcca      60
tccttttttt ttattaaaga gttgcaaggt attcaactt tatgagaatt tgtgtgcaaa       120
tgaaggctct ccttattttg ctaaagtaga cacagccta atgatgagag atctttccgc       180
tcattgccca ttcaaataca attgtagatc gaagccggcc ttgtcaggtt gagaaaaagt      240
gaatctctaa catccaggac gtgcctgtct actttcagag aattgcatcc aatcaccccc      300
agggaattca gctaatgtct ccatctccac ccagacaagg gagagaaaga aatcaaacgt      360
ggtatggcaa gctgacttct tatgagaatg tttaagagga aaaaaaaaaa aaaaaagaca      420
gtggaatgtt cttgaattga tggcagcaga ggctttctc agtggggaaa gcaaactaac       480
tgcaagaatt gaggattttc taaaaggttc ggcagaactt cttact                     526
```

<210> SEQ ID NO 2
<211> LENGTH: 550
<212> TYPE: DNA
<213> ORGANISM: Homo sapiens

<400> SEQUENCE: 2

```
tgaaacccc tcatctccct ctctcagcct tccctggcc tccaatttaa attatgcagc        60
aatccttttt tattaaaggg ttgcagggaa tccgagtttt atgagcattt gtgtgcaaat      120
gaaggctctc cttattttgc taaagtagaa gcaagcttaa tgatgagaga tctttccgct      180
cattgcccat tcaaatacaa ttgtagatcg aagccggcct tgtcacgttg agaaaaagtg     240
aatttctaac atccaggacg tgcctgtcta ctttcagtga attgcatcca atcaccccca     300
gggaattcag ctaatgtctc catctctacc cggacaaggg agagaaagaa atcaaacatg      360
gtgccacaaa ctgacttaat atgaaaatgt ttaaaaggaa agaaaaagca gagttttctc     420
aaattgattg ttgtagagtt ttttgttttg ttttgtttgt ttgtttgttt tttgtttgtt     480
tgtttgtttg tgacaaagct aactggaagg attggagatt ttccacagag gtccgggaaa     540
```

```
acttttatg                                                              550

<210> SEQ ID NO 3
<211> LENGTH: 342
<212> TYPE: DNA
<213> ORGANISM: Mouse

<400> SEQUENCE: 3 tttttatta aagagttgca aggtattcaa cttttatgag aatttgtgtg caaatgaagg         60
ctctccttat tttgctaaag tagacacagc cttaatgatg agagatcttt ccgctcattg       120
cccattcaaa tacaattgta gatcgaagcc ggccttgtca ggttgagaaa aagtgaatct       180
ctaacatcca ggacgtgcct gtctactttc agagaattgc atccaatcac ccccagggaa       240
ttcagctaat gtctccatct ccacccagac aagggagaga aagaaatcaa acgtggtatg       300
gcaagctgac ttcttatgag aatgtttaag aggaaaaaaa aa                         342

<210> SEQ ID NO 4
<211> LENGTH: 342
<212> TYPE: DNA
<213> ORGANISM: Homo sapiens

<400> SEQUENCE: 4 tttttatta aagggttgca gggaatccga gttttatgag catttgtgtg caaatgaagg         60
ctctccttat tttgctaaag tagaagcaag cttaatgatg agagatcttt ccgctcattg       120
cccattcaaa tacaattgta gatcgaagcc ggccttgtca cgttgagaaa aagtgaattt       180
ctaacatcca ggacgtgcct gtctactttc agtgaattgc atccaatcac ccccagggaa       240
ttcagctaat gtctccatct ctacccggac aagggagaga aagaaatcaa acatggtgcc       300
acaaactgac ttaatatgaa aatgtttaaa aggaaagaaa aa                         342

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence:PRIMER

<400> SEQUENCE: 5
aaggaaaaaa gcggccgcgg ttacaccaga agcaccc                                37

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:PRIMER

<400> SEQUENCE: 6
gcgggatcca gtaagaagtt ctgccgaac                                         29
```

LENS TRANSCRIPTIONAL CONTROL ELEMENTS AND METHODS OF USE THEREOF

CROSS-REFERENCE TO RELATED APPLICATIONS

The present Application is a non-provisional application claiming the priority of copending provisional U.S. Ser. No. 60/084,588 filed May 7, 1998, the disclosure of which is hereby incorporated by reference in its entirety. Applicants claim the benefits of this Application under 35 U.S.C. §119(e).

GOVERNMENTAL SUPPORT

The research leading to the present invention was supported, at least in part, by a grant from the National Institutes of Health Grant Nos. EY11234 and HD32105. Accordingly, the Government may have certain rights in the invention.

FIELD OF THE INVENTION

The invention relates generally to transcriptional control elements that are tissue specific. More particularly, the invention relates to nucleic acids that contain tissue-specific transcriptional control elements. The invention also relates to methods of using these control elements including for the identification modulators of tissue-specific protein expression.

BACKGROUND OF THE INVENTION

The transcription factor Pax-6 is known to have a critical role in development of the eye in a number of species [Quiring et al., *Science* 265:785–789 (1994)]. In Drosophila, homozygous mutation of the Pax-6 orthologue eyeless results in missing eye structures. In humans, heterozygous Pax-6 mutations give the ocular defects aniridia (iris hypolasia [Jordan et al., *Nat. Genet.* 1:328–332 (1992)]) and Peters' anomaly (a combination of iris hypolasia and lens-corneal epithelium attachment [Hanson et al., *Nature Genetics*, 6:168–173 (1994)]). Analogous defects are seen in the Small eye mice, also heterozygous for a Pax-6 mutation [Hill et al., *Nature* 354:522–525 (1991)]. Homozygous mutation in mice is lethal and results in severe cranio-facial abnormalities including absence of eyes [Hill et al., *Nature* 354:522–525 (1991)].

Gain-of-function experiments also demonstrate a central role for Pax-6 in development of the eye. In Xenopus, expression of the transcription factor Pax-6 directs induction of the lens [Altmann et al., *Dev. Biol.* 185:119–123 (1997); U.S. application Ser. No. 08/846,463 filed May 1, 1997 hereby incorporated by reference in its entirety]. Analogously, overexpression of Drosophila Pax-6 in imaginal discs results in the development of ectopic compound eyes [Gehring et al., *Genes to Cells* 1: 11–15 (1996)]. Remarkably, this activity can be mimicked by Pax-6 from a number of species including, squid [Tomarev et al., *Proc. Natl. Acad. Sci. U.S.A.* 94:2421–2426 (1997)] and ascidian [Glardon et al., *Development* 124:817–825 (1997)] arguing that Pax-6 function has been conserved across more than 40 million years of evolution [Gehring et al., *Genes to Cells* 1:11–15 (1996)].

In animal cap experiments, Pax-6 can induce the expression of the lens-specific marker βB1-crystallin without inducing the general neural marker NCAM. Ectopic Pax-6 expression also results in the formation of ectopic lenses in whole embryos indicating that in vertebrates, as well as Drosophila [Halder, et al., *Science*, 267:1788–1792 (1995)], Pax-6 can direct the development of major components of the eye. According to NCAM staining, ectopic lenses formed in the whole embryo are only sometimes associated with neural tissue. Furthermore, treatments giving rise to anterior neural tissue result in the expression of both βB 1-crystallin and Pax-6.

In the mouse, Pax-6 has a complex pattern of expression that includes multiple components of the developing eye, as well as neural tube, forebrain neuroepithelium, olfactory epithelium and bulbs, pancreas and pituitary [Grindley et al., *Development* 121:1433–1422 (1995); Walther et al., *Development* 113:1435–1449 (1991)]. In the eye, Pax-6 is expressed in the presumptive and mature lens, retina and corneal epithelium [Grindley et al., *Development* 121:1433–1442 (1995); Walther et al., *Development* 113:1435–1449 (1991)]. This expression pattern is conserved in different vertebrate species including in Xenopus [Li et al., *Development*, 124:603–615 (1997)] and chick [Li et al., *Dev. Biol.*, 162:181–194 (1994)].

Although it would be valuable to be able to express selected proteins solely in the lens and/or corneal epithelium, heretofore no lens and/or corneal epithelium specific transcriptional control element has been identified. Therefore, there is a need to identify such a lens and/or corneal epithelium transcriptional control element. Furthermore, there is a need to identify agents that can modulate lens and/or corneal epithelium development including naturally occurring transcription factors.

The citation of any reference herein should not be construed as an admission that such reference is available as "Prior Art" to the instant application.

SUMMARY OF THE INVENTION

The present invention provides a lens transcription control element that can be used to identify factors, both naturally occurring and synthetic, that will modulate lens and/or corneal epithelium development and function. This lens transcription control element can be used to direct transcription in the lens and/or corneal epithelium The present invention therefore provides a recombinant nucleic acid comprising a lens and corneal epithelium specific transcriptional control element (LCE) that hybridizes with a nucleic acid having the nucleotide sequence of SEQ ID NO:1 or a functional derivative thereof. In another embodiment the recombinant nucleic acid contains a LCE that hybridizes with a nucleic acid having the nucleotide sequence of SEQ ID NO:3. In a preferred embodiment of this type the hybridization is performed under standard conditions. In a more preferred embodiment the hybridization is performed under stringent conditions.

The present invention also provides a recombinant nucleic acid comprising a lens and corneal epithelium specific transcriptional control element (LCE) that hybridizes with a nucleic acid having the nucleotide sequence of SEQ ID NO:2 or a functional derivative thereof. In another embodiment the recombinant nucleic acid contains a LCE that hybridizes with a nucleic acid having the nucleotide sequence of SEQ ID NO:4. In a preferred embodiment of this type the hybridization is performed under standard conditions. In a more preferred embodiment the hybridization is performed under stringent conditions.

In one embodiment, the lens specific transcriptional control element contains between 100 to 800 nucleotides. In a preferred embodiment the LCE contains 200 to 600 nucleotides. In a more preferred embodiment the LCE contains 250 to 450 nucleotides. In a particular embodiment, the LCE contains 341 nucleotides. In a preferred embodiment of this type, the LCE has a nucleotide sequence of SEQ ID NO:3. In another embodiment, the LCE has a nucleotide sequence of SEQ ID NO:4.

The LCE of the present invention is preferably a vertebrate control element. In one such embodiment the LCE is a xenopus control element. In an alternative embodiment the LCE is a mammalian control element. In one such embodiment, the mammalian control element is a murine control element. In a preferred embodiment of this type the LCE is a Pax-6 conserved element (PACE) having the nucleotide sequence of SEQ ID NO:1. In an alternative embodiment the PACE has the nucleotide sequence of SEQ ID NO:3. In another such embodiment the mammalian control element is a human control element. In a preferred embodiment of this type the LCE is a Pax-6 conserved element (PACE) having the nucleotide sequence of SEQ ID NO:2. In an alternative embodiment the PACE has the nucleotide sequence of SEQ ID NO:4.

The present invention also includes nucleotide probes that hybridize with a nucleic acid having the nucleotide sequence of SEQ ID NO:1. In a related embodiment the present invention provides a nucleotide probe that hybridizes with a nucleic acid having the nucleotide sequence of SEQ ID NO:2. In yet another embodiment the nucleotide probe hybridizes with the nucleotide sequence of SEQ ID NO:3. In still another embodiment the nucleotide probe hybridizes with the nucleotide sequence of SEQ ID NO:4. In a preferred embodiment the hybridization is done under standard hybridization conditions. In a more preferred embodiment the hybridization is performed under stringent conditions.

The present invention further provides a recombinant DNA molecule that comprises a recombinant nucleic acid that contains an LCE of the present invention and a coding sequence operatively linked to the recombinant nucleic acid. In a preferred embodiment of this type the LCE has the nucleotide sequence of SEQ ID NO:1. In a related embodiment, the LCE has the nucleotide sequence of SEQ ID NO:2. In still another embodiment the LCE has the nucleotide sequence of SEQ ID NO:3. In yet another embodiment the LCE has the nucleotide sequence of SEQ ID NO:4.

The recombinant DNA molecules of the present invention can further comprise a promoter or a minimal promoter that functions in conjunction with the LCE of the recombinant nucleic acid. In a preferred embodiment of this type, the LCE is adjacent to the promoter or minimal promoter. The present invention further provides expression vectors which comprise the recombinant DNA molecules of the present invention. The coding sequences contained in the expression vectors can encode a marker protein or a therapeutic protein. In one embodiment the marker protein is green fluorescent protein. In another embodiment the marker protein is β-galactosidase.

The present invention also provides transgenic animals which comprise cells containing an expression vector of the present invention. In a preferred embodiment the transgenic anal is a mammal. In a more preferred embodiment the mammal is a mouse. Such expression vectors comprise a coding sequence that is operatively linked to a promoter or a minimal promoter and under the control of an LCE or PACE of the present invention.

Another aspect of the present invention provides methods of expressing the coding sequence contained in the expression vectors of the present invention in a cell.

The present invention further provides a method of directing the expression of the coding sequence contained within an expression vector of the present invention to the presumptive lens ectoderm while excluding expression in neural components of the eye. In one such embodiment the expression vector is placed into an animal zygote. In a preferred embodiment of this type placing of the expression vector into the animal zygote is performed by injection. In a particular embodiment the animal zygote is a xenopus zygote. In another such embodiment the animal zygote is a mammalian zygote. In a preferred embodiment of this type the mammalian zygote is a murine zygote.

In addition, the present invention provides a method of detecting the lens and/or corneal epithelium specific transcription of an mRNA encoding a marker protein in an animal zygote. In one such embodiment, an expression vector of the present invention is placed into an animal zygote. The expression vector contains a coding sequence that is operatively linked to a promoter or a minimal promoter and under the control of an LCE of the present invention. The coding sequence encodes a marker protein. The zygote is allowed to develop, and an mRNA encoding the marker protein is transcribed. The transcription of the mRNA encoding the marker protein is then detected. In a related embodiment, the mRNA is expressed and the step of detecting the transcription of the mRNA encoding the marker protein is performed by detecting the marker protein.

The present invention further provides a method of identifying an agent or drug that modulates lens and/or corneal epithelium development. In one such embodiment, an expression vector of the present invention is placed into an animal zygote in the presence of the potential drug or agent. The expression vector contains a coding sequence operatively linked to a promoter or a minimal promoter and under the control of an LCE of the present invention. In a particular embodiment the minimal promoter is from the hsp68 gene. The coding sequence encodes a marker protein.

The zygote is allowed to develop under conditions in which in the absence of the potential agent or drug, an mRNA encoding the marker protein is transcribed. The amount of transcription of the mRNA encoding the marker protein is determined. A potential agent or potential drug is identified as an agent or drug when the amount of transcription of the mRNA encoding the marker protein in the presence of the potential agent is different than in its absence. An agent or drug so identified is further identified as an agonist if the amount of transcription of the mRNA encoding the marker protein in the presence of the agent or drug is greater than in its absence. Analogously, the agent or drug is further identified as an antagonist when the amount of transcription of the mRNA encoding the marker protein in the presence of the potential drug or agent is less than in its absence. In another particular embodiment the agent that is identified, is a transcription factor. In yet another embodiment, the mRNA that is transcribed is also expressed and the step of determinig the amount of transcription of mRNA encoding the marker protein is performed by determining the amount of the marker protein.

The present invention further provides a method of identifying a transcription factor that modulates lens and/or corneal epithelium development. In one such embodiment, an expression vector of the present invention is placed into an animal zygote in the presence of a potential transcription factor. Such an expression vector comprises a coding sequence that is operatively linked to a promoter or preferably a minimal promoter and under the control of an LCE or PACE of the present invention. In one particular embodiment the minimal promoter is from the hsp68 gene.

The zygote is allowed to develop under conditions where the transcription of an mRNA encoding the marker protein requires the presence of the transcription factor. The transcription of the mRNA encoding the marker protein is then detected. A potential transcription factor is identified as a transcription factor that modulates lens and/or corneal epithelium development when the transcription of the mRNA encoding the marker protein is detected in the presence of the potential transcription factor. In a related embodiment, the mRNA that is transcribed is also expressed and the step of detecting the transcription of the mRNA encoding the marker protein is performed by detecting the marker protein.

The present invention further includes a method of identifying a transcription factor that modulates a gene which comprises an LCE or PACE of the present invention. In one such embodiment an expression vector of the present invention is placed into a cell in the presence of a potential transcription factor. The expression vector comprises a coding sequence encoding a marker protein that is operatively linked to a promoter or a minimal promoter and under the control of the LCE. In a particular embodiment of this type, the minimal promoter is from the hsp68 gene. The cell is cultured in an appropriate cell culture medium under conditions that provide for transcription of an mRNA encoding the marker protein by the cell, but requires the presence of the transcription factor. The transcription of the mRNA encoding the marker protein is detected and a potential transcription factor is identified as a transcription factor that modulates the gene when the transcription of the mRNA encoding the marker protein is detected. In a related embodiment the mRNA that is transcribed is also expressed, and the step of detecting the transcription of the mRNA encoding the marker protein is performed by detecting the marker protein.

The present invention further provides a method of identifying a binding partner for an LCE or PACE of the present invention. In one such embodiment, a candidate binding partner is contacted with a recombinant nucleic acid which comprises an LCE or PACE of the present invention. The binding of the candidate binding partner with the recombinant nucleic acid is detected, and a candidate binding partner is identified as a binding partner when the candidate binding partner is detected as binding to the recombinant nucleic acid. In one such embodiment the LCE has the nucleotide sequence of SEQ ID NO:1. In another such embodiment the LCE has the nucleotide sequence of SEQ ID NO:2. In still another embodiment the LCE has the nucleotide sequence of SEQ ID NO:3. In yet another such embodiment the LCE has the nucleotide sequence of SEQ ID NO:4.

In a related embodiment, the method of identifying a binding partner for an LCE or PACE of the present invention comprises placing a recombinant nucleic acid comprising an LCE or PACE of the present invention on a solid support. The solid support is contacted with a candidate binding partner under conditions in which a binding partner can bind to the recombinant nucleic acid. A solid support is washed and candidate binding partners that do not bind the recombinant nucleic acid are removed. The candidate binding partner bound to the solid support is detected. A candidate binding partner is identified as a binding partner if it binds to the solid support. In a preferred embodiment of this type, the candidate binding partner is a potential transcription factor for a gene that comprises the LCE or PACE. In this case, the binding partner that is identified is a transcription factor for the gene which comprises the LCE or PACE. In one such embodiment, the solid support is a nitrocellulose filter. In one such embodiment the LCE has the nucleotide sequence of SEQ ID NO:1. In another such embodiment the LCE has the nucleotide sequence of SEQ ID NO:2. In still another embodiment the LCE has the nucleotide sequence of SEQ ID NO:3. In yet another such embodiment the LCE has the nucleotide sequence of SEQ ID NO:4.

These and other aspects of the present invention will be better appreciated by reference to the following drawings and Detailed Description.

BRIEF DESCRIPTION OF THE DRAWINGS

FIG. 1 shows the alignment of mouse (SEQ ID NO:1) and human (SEQ ID NO:2) Pax-6 gene sequences. Nucleotide identities between mouse and human Pax-6 gene sequences are indicated by the boxing. The 341 basepair region of high percentage identity for the mouse (SEQ ID NO:3) and human (SEQ ID NO:4) is indicated by the arrows. Sequence numbering is indicated for the human sequence on the lower line (accession number Z95332) and for the mouse sequence on the upper line. The regions of complementarity for oligonucleotides used in the construction of reporter plasmids are overlined, see, Example below.

FIG. 2 contains a summary of the expression patterns of reporter constructs carrying different regions of the Pax-6 gene. The basic structure of the Pax-6 gene is indicated in the top row having the Gene construct name Pax-6. The approximate locations of the Pax-6 conserved element, PACE, (CE) is indicated by the red box. Reporter constructs carry a transcriptional start-point either from the Pax-6 gene (black arrow) or from the hsp68 gene (gray arrow). In each construct, the start-point of transcription is immediately upstream of the open reading frame for β-galactosidase (lacZ, blue box) which in turn is upstream of the splicing and polyadenylation signals from the Simian virus 40 small t gene (SV40 t) [Song et al., *Development* 122:627–635 (1996)]. For the P6-3.9–3.5 construct, a minimal promoter from the mouse hsp68 gene was employed. All other constructs use the Pax-6 gene P0 promoter. The expression pattern resulting from the generation of transgenic mice is summarized in the columns at the right, a "+" indicating strong expression, a "+/−" indicating weak expression and a "−" indicating no detectable expression.

FIGS. 3A–3D show whole mount X-gal staining for transgenic mice generated with construct P6-5.0. Staining is observed in the presumptive lens ectoderm (ple) at E8.75 (FIG. 3A) and E9.5 (FIG. 3B) in the lens pit (lp) at E10.5 (FIG. 3C) and in the lens and future corneal epithelium (cor) at E12.5 (FIG. 3D). At each developmental stage shown, X-gal labeling is also observed in the viscera (arrowheads). The transgenic mice generated with the P6-3.9 construct show strong X-gal staining in the lens pit (lp) of the developing eye and weak staining in a discrete component of the viscera (FIG. 3E, arrowhead). In FIG. 3F, the P6-3.9–3.5 construct show X-gal staining in the lens pit (lp) and neural tube (nt). Staining in the neural tube is typical of the activity of the minimal promoter for the mouse hsp68 gene [Song et al., *Development* 122:627–635 (1996)]. FIG. 3G shows the pattern of X-gal staining at E10.5 for the P6-3.9–3.5 construct in the region of the lens pit (lp) and first branchial arch (1ba). Staining is observed at the rostral edge of the first branchial arch (FIG. 3G, arrowheads). FIGS. 3H–3K show histological sections through the eye at various stages of development. In all cases, rostral is to the left, caudal to the right. At E9.5, (FIG. 3H) X-gal staining is restricted to the presumptive lens ectoderm (ple) overlying the optic vesicle (ov). At E10.5, (FIG. 3I) staining is seen in the invaginating lens pit (lp) and in the surface ectoderm (ect) but not presumptive retina (pr). At E11.0, (FIG. 3J) lacZ expression is detected in the surface ectoderm (ect) and throughout the lens vesicle (lv). At E12.5, (FIG. 3K) when the primary lens fiber cells (plfc) are elongating and filling the volume of the lens vesicle, lacZ expression is seen primarily in the lens epithelium (le) but is also observed in the future corneal epithelium (cor). In all sections, labeling is not observed in the neurally-derived optic vesicle (ov), optic stalk (os), presumptive retina (pr) and presumptive retinal pigmented epithelium (rpe).

DETAILED DESCRIPTION OF THE INVENTION

Figure 3:
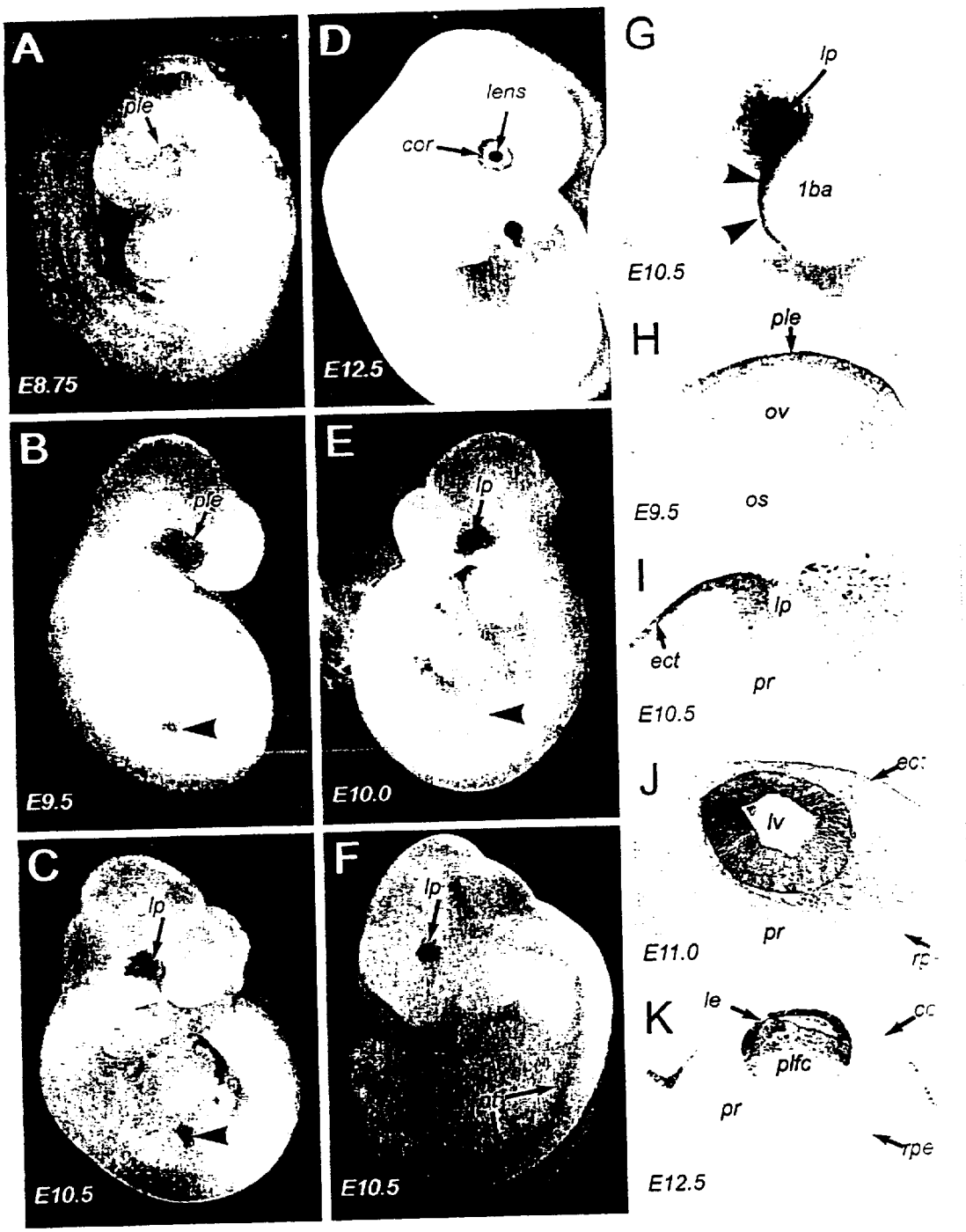
FIGS. 3A–3K demonstrates that PACE supports reporter construct expression in lens and corneal epithelium

The present invention provides nucleic acids containing transcriptional control elements. In one aspect of the invention the transcriptional control element is specific for a Pax-6 gene. The present invention, therefore, provides a Pax-6 conserved element (PACE) that has transcriptional control of the Pax-6 gene. In another aspect, the present invention provides a PACE that is a transcriptional control element for lens and corneal epithelium (LCE).

In one embodiment of the present invention, the PACE comprises a short segment of the mouse Pax-6 gene 5' flanking region that is both necessary and sufficient for reporter construct expression in components of the eye derived from non-neural ectoderm. In a particular embodiment of this type the PACE has a highly conserved nucleotide sequence over 341 basepairs (SEQ ID NO:3) and is located approximately 3.5 kilobases upstream of the startpoint for transcription from the most proximal promoter (P0) of the murine Pax-6 gene. The level of conservation between human and mouse Pax-6 genes in this region is 93%. In one embodiment of the present invention the PACE is combined with its natural promoter. In another embodiment the PACE is combined with a heterologous minimal promoter. In a particular embodiment the minimal promoter is from the hsp68 gene. In one embodiment, the PACE is used to direct protein expression to a region of surface ectoderm overlying the optic cup beginning at E8.5–E9.0 (12–14 somites) in murine zygotes, and expression is restricted to the lens (primarily the lens epithelium) and the corneal epithelium. In such an embodiment, the PACE is used to direct transgene expression to the presumptive lens ectoderm while excluding expression in neural components of the eye.

Thus, the LCEs of the present invention can be used to define the crucial steps in lens and/or corneal epithelium development. For example, since the LCE "PACE" is necessary and sufficient for expression in the presumptive lens ectoderm, it can be used to analyze lens development and/or corneal epithelium development in transgenic animals. In one such embodiment, the transgenic animal is a mouse. In another embodiment, the PACE controls the expression of a reporter gene.

In addition, the PACE represents an essential component of the lens and corneal epithelium development pathway. Identifying the transcription factors that normally interact with this element in regulating expression of Pax-6 in ectoderm therefore will yield additional components that play a central function in lens and/or corneal epithelium development. Still another aspect of the present invention provides methods for identifying binding partners, and agents (including transcription factors) that can interact with the LCEs of the present invention.

Nucleic Acids Containing a PACE and/or a LCE

The present invention contemplates obtaining a nucleic acid containing a PACE and/or LCE or functional derivative thereof, from any eukaryotic source, preferably a vertebrate source, and more preferably a mammalian source.

In accordance with the present invention there may be employed conventional molecular biology, microbiology, and recombinant DNA techniques within the skill of the art, including the use of genomic databases to identify corresponding nucleotide sequences. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

As used herein an "ectopic lens" is an otherwise natural lens which is produced outside of the location that it is normally is formed.

As used herein the "lens development pathway" in a vertebrate encompasses all of the factors and steps involved in the development of a vertebrate lens starting with the initial induction of an ectodermal cell to begin the process up to the ultimate formation of the mature vertebrate lens.

As used herein the "corneal epithelium pathway" in a vertebrate encompasses all of the factors and steps involved in the development of a vertebrate corneal epithelium starting with the initial induction of an ectodermal cell to begin the process up to the ultimate formation of the mature vertebrate corneal epithelium.

As used herein, "Pax-6" is meant to include all active forms of the highly conserved Pax-6 protein including genetically engineered and natural occurring mutants, fusion proteins thereof, and active fragments thereof, wherein an active form of Pax-6 can function as a transcription factor during lens development in an ectodermal cell. In a preferred embodiment the Pax-6 is a vertebrate Pax-6.

As used herein, a "Pax-6" gene, or "Pax-6" nucleic acid, or "Pax-6" RNA encodes a Pax-6 protein as defined above.

As used herein, the term "gene" refers to a nucleotide sequence that contains a coding sequence and preferably at least one transcriptional control sequence.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

Transcriptional and translational control sequences or elements are DNA regulatory sequences, such as promoters, enhancers, terminators, and the like, that provide for the expression of a coding sequence in a host cell. In eukaryotic cells, polyadenylation signals are control sequences.

A coding sequence is "under the control" of a transcriptional control element if that control element controls the transcription of the coding sequence with respect to place (e.g., tissue type) and/or time (e.g., developmental stage).

A coding sequence is "operatively linked to" a promoter if the binding of RNA polymerase to the promoter can lead to the transcription of the coding sequence into mRNA. The mRNA may then be spliced (if necessary) and translated into the protein encoded by the coding sequence.

A "promoter" is a DNA regulatory region capable of binding RNA polymerase and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase.

As used herein, a "minimal promoter" is a portion of a promoter that in combination with an LCE or a PACE of the present invention allows the transcription of a coding sequence that is operatively linked to the minimal promoter. The use of the P0 murine Pax-6 gene promoter and the minimal hsp68 promoter are described in the Example below.

As used herein, the term "PACE" is used interchangeably with the phrase, "Pax-6 conserved element", and is used to describe a transcription control element that plays a role in the control of the transcription of a Pax-6 gene. A PACE that contains the nucleotide sequence of SEQ ID NO:1 is exemplified below. In another embodiment, a PACE contains the nucleotide sequence of SEQ ID NO:2. In still another embodiment a PACE contains the nucleotide sequence of SEQ ID NO:3. In yet another embodiment a PACE contains the nucleotide sequence of SEQ ID NO:4.

A "PACE" of the present invention can be obtained from any eukaryotic source, preferably a vertebrate source, and more preferably a mammalian source. A PACE of the present invention can be combined with its natural promoter, another promoter, or preferably a minimal promoter to control the transcription of a coding sequence that is operatively linked to the promoter or minimal promoter. In a preferred embodiment, the PACE is adjacent to the promoter or minimal promoter. Nucleotide modifications and truncations of the PACEs of the present invention which lead to functionally improved or equivalent control elements are also included in the present invention.

As used herein, the term "LCE is used interchangeably with the phrase, "lens and corneal epithelium transcriptional control element", and is used to describe a transcription control element that plays a role in the control of the transcription of a gene in the lens and/or corneal epithelium. When the LCE is placed into a lens and not into the corneal epithelium, the LCE can act as a transcriptional control element for the lens alone. Similarly when a LCE is placed into the corneal epithelium and not into the lens, the LCE can act as a transcriptional control element for the corneal epithelium alone. However, when the LCE is placed into both the lens and the corneal epithelium, e.g., into a transgenic animal (see Example below), the LCE acts as a transcriptional control element in both the lens and the corneal epithelium. An "LCE" of the present invention can be obtained from any eukaryotic source, provided the eukaryote encodes lens or corneal epithelium proteins, preferably the eukaryotic source is a vertebrate source, and more preferably a mammalian source. A LCE of the present invention can be combined with its natural promoter, another promoter, or a minimal promoter to control the transcription of a coding sequence operatively linked to the promoter or minimal promoter. In a particular embodiment, the minimal promoter is from the hsp 68 gene. In a preferred embodiment, the LCE is adjacent to the promoter or minimal promoter. Nucleotide modifications and truncations of the LCEs of the present invention which lead to functionally improved or equivalent control elements are also included in the present invention.

A "vector" is a replicon, such as plasmid, phage, virus, or cosmid, to which another DNA segment may be attached so as to bring about the replication of the attached segment.

A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

As used herein a "marker" is an indicator, whose presence or absence can be used to distinguish the presence or absence of a particular nucleic acid and preferably the corresponding presence or absence of a larger DNA which contains and/or is linked to the specific nucleic acid. In a preferred embodiment the marker is a protein or a gene encoding the protein, and thus can be more specifically termed a "marker protein" or a "marker gene". The term "marker" (and thus marker protein or marker gene) is meant to be used extremely broadly and includes fluorescent proteins such as green fluorescent protein, enzymes such as luciferase, and further includes drug resistant proteins, whose presence or absence may not solely be regarded as a means to detect cells that contain the drug resistance protein; and/or the genes that encode such proteins. However, drug resistance proteins and/or their corresponding genes can allow the preferential growth of cells that contain the drug resistant gene (or alternatively allow the counter-selection of cells that do not contain the drug resistant gene) and therefore bestow a type of selectable distinction which is meant to fall within the present definition of a marker.

The term "a gene which encodes a marker protein" is used herein interchangeably with the term "marker protein gene" and denotes a nucleic acid which encodes a marker protein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–10.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 24 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences (e.g., including a PACE or LCE). The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

The term "corresponding to" is used herein to refer similar or homologous sequences, whether the exact position is identical or different from the molecule to which the similarity or homology is measured. The term "corresponding to" refers to the sequence similarity in nucleotide sequences in the absence of gaps in the nucleotide sequence.

A gene containing a PACE or an LCE can be isolated from any genomic source. In the Example below, the Pax-6 gene was isolated from a genomic library, i.e., a murine library generated from the 129sv strain in the λFIXII vector (Stratagene). A PCR-derived probe from a region just upstream of the relevant promoter, e.g., the P0 promoter, can be used. Several λ clones can then isolated and restriction mapped. In the Example below, the λ clones were found to span a 15 kilobase region that included at least 7 kilobases 5' of the P0 promoter. The 7 kilobase region upstream of the promoter can then be subcloned and sequenced (e.g., using automated techniques). Alignments to identify conserved regions of the Pax-6 gene 5' flanking sequence can then be performed using the Lasergene software suite, for example.

The production and use of derivatives and analogs related to a PACE and an LCE of the present invention are within the scope of the present invention. In a specific embodiment, the derivative or analog is functionally active, i.e., capable of playing a role in the control of the transcription of a coding sequence operatively linked to a promoter or minimal promoter when the derivative or analog is combined with the promoter or minimal promoter. For example, PACE derivatives can be made by altering encoding nucleic acid sequences by substitutions, additions or deletions that provide for functionally equivalent molecules. Preferably, derivatives are made that have enhanced or increased functional activity relative to the native PACE.

The nucleic acids that contain the PACE or LCE derivatives and analogs of the invention can be produced by various methods known in the art. The sequence can be cleaved at appropriate sites with restriction endonuclease(s), followed by further enzymatic modification if desired, isolated, and ligated in vitro. Alternatively the PACE or LCE can be prepared de novo using a nucleotide synthesizer for example.

The nucleotide sequence containing a PACE or LCE, derivative or analog thereof, can be inserted directly into an ectodermal cell or alternatively into an appropriate expression vector, i.e., a vector which contains a promoter or a minimal promoter required for the transcription and translation of an inserted protein-coding sequence. Thus, the nucleic acid containing the PACEs or LCEs of the present invention can be combined with a promoter and a coding sequence operatively linked to the promoter in an expression vector of the invention. An expression vector also can include a replication origin. Additional transcriptional and translational signals can be provided on a recombinant expression vector, or they may be supplied by the native gene encoding the protein of interest. The coding sequence can be expressed in an ectodermal cell or a mature lens and/or corneal epithelium cell for example.

In the example below, lacZ reporter constructs were generated using the plasmid phspPTlacZpA. phspPTlacZpA is a reporter plasmid that contains promoter sequences (−664 to +224 relative to the start-point of transcription) from the mouse hsp68 gene and includes the translational start codon fused in-frame to a lacZ open reading frame. For the P6-3.9–3.5 construct, the PACE was amplified by PCR and subcloned upstream of the minimal hsp68 promoter. For other reporter constructs, the hsp68 promoter was eliminated and a region of the Pax-6 gene that included the P0 promoter (to the BglII site in the 5' untranslated region) was subcloned upstream of lacZ.

Vectors may be introduced into the desired host cells and zygotes, by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990). In the Example below, reporter constructs containing a nucleic acid encoding a marker protein operatively linked to a promoter and under the control of a PACE were injected into a mouse zygote.

Labels

Nucleic acids including probes that can hybridize with the PACEs, LCEs and derivatives thereof, as well assorted reagents and markers employed to monitor the transcriptional control of the PACEs and LCEs and/or lens and/or corneal epithelium development may be appropriately labeled. Suitable labels include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety such as a green fluorescent protein or a modified green fluorescent protein as described in U.S. Pat. No. 5,625,048, Issued Apr. 29, 1997 and WO 97/26333 Published Jul. 24, 1997 hereby incorporated by reference in their entireties, indirect labels comprising enzymes can also be used according to the present invention. Various types of enzyme linked immunoassays are well known in the art, for example, luciferase, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

Proteins, including antibodies, can be labeled by metabolic labeling. Metabolic labeling occurs during in vitro incubation of the cells that express the protein in the presence of culture medium supplemented with a metabolic label, such as [$^{35}S$]-methionine or [$^{32}P$]-orthophosphate. In addition to metabolic (or biosynthetic) labeling with [$^{35}S$]-methionine, the invention further contemplates labeling with [$^{14}C$]-amino acids and [$^3H$]-amino acids (with the tritium substituted at non-labile positions). In addition a protein can be labeled with a FLAG-tag, an eight amino acid epitope [Pricket, et al., *Biotechniques*, 7:580–589 (1989)].

Screening For Agents That Modulate Lens Development

The present invention contemplates screens for an agent that modulates lens and/or corneal epithelium development. In one such embodiment, an expression vector containing an LCE (or PACE) and a promoter (or minimal promoter) upstream of a coding sequence, that is under the control of the LCE and operatively linked to the promoter (or minimal promoter), is placed into an animal zygote in the presence of a potential agent. The zygote is allowed to develop under conditions in which in the absence of the potential agent, the coding sequence is transcribed. The amount of transcription of the coding sequence in the lens and/or corneal epithelium is determined and an agent is identified when the amount of transcription of the coding sequence in the presence of the potential agent is different than in its absence. The vectors may be introduced by any of the methods described above. In a preferred embodiment the vector is placed into the zygote by injection.

The present invention also provides alternative methods for identifying an agent that modulates lens and corneal epithelium development. In one such embodiment, an expression vector containing a coding sequence encoding a marker protein operatively linked to a minimal promoter and under the control of a LCE or PACE is placed into a cell in the presence of a potential agent. The cell is cultured in an appropriate cell culture medium under conditions that provide for transcription of the coding sequence by the cell in the absence of the potential agent. The amount of transcription of the coding sequence is determined. An agent is identified when the amount of transcription of the coding sequence in the presence of the potential agent is different than in its absence.

In a related embodiment the coding sequence is transcribed and expressed and the step of determining the amount of transcription of the coding sequence is performed by determining the amount of expression of the marker protein. In this case, the coding sequence can encode a marker protein such as green fluorescent protein or luciferase. In a preferred embodiment of this type the coding sequence encodes LacZ.

When the amount of transcription of the coding sequence in the presence of the agent is greater than in its absence, the agent is identified as an agonist of lens and corneal epithelium development, whereas when the amount of transcription of the coding sequence in the presence of the agent is less than in its absence, the agent is identified as an antagonist of lens and corneal epithelium development. As any person having skill in the art would recognize, such determinations as these and those described below may require some form of statistical analysis, which is well within the skill in the art.

The present invention further provides a method of identifying a transcription factor that can modulate lens and/or corneal epithelium development. In one such embodiment, an expression vector containing a coding sequence operatively linked to a minimal promoter and under the control of an LCE or a PACE, is placed into a cell in the presence of the potential transcription factor. The cell is cultured in an appropriate cell culture medium under conditions that require the presence of the transcription factor for the transcription of the coding sequence by the cell. The transcription of the coding sequence is detected. A potential transcription factor is identified as a transcription factor that modulates lens and/or corneal epithelium development when the transcription of the coding sequence is detected in the presence of the potential transcription factor. As above, the transcription of the coding sequence can also be monitored by detecting the expression of the protein encoded by the coding sequence.

The present invention further provides methods of identifying a binding partner for the LCEs and PACEs of the present invention.

One such embodiment includes contacting a candidate binding partner with the PACE or LCE and then detecting the binding. A binding partner is identified when the binding of the candidate binding partner with the PACE or LCE is detected. One preferred embodiment of this type places the nucleic acid on a solid support, such as a nitrocellulose filter. A binding partner identified in this manner can be further tested as a potential drug or agent, or alternatively as a potential transcription factor.

The present invention further provides methods of using the vectors of the present invention to detect the lens and corneal epithelium specific transcription of a coding sequence encoding a marker protein in an animal zygote. The expression vector is placed into the animal zygote by one of the methods included above, and the zygote is allowed to develop. The marker protein is transcribed and the transcription of the mRNA encoding the marker protein can be detected. In a related embodiment, the mRNA is also expressed, and the detection of the transcription of mRNA is performed by detecting the expression of the marker protein. In one particular embodiment, the marker protein is visible (e.g. colored or fluorescent) and the expression of the marker protein can be detected by viewing the color of lenses of the animal.

Potential agents and drugs can be obtained from many sources. Natural effectors found in the ectodermal cell can be fractionated and tested using standard effector assays as exemplified above. Thus an identified agent can be a naturally occurring transcription factor. Alternatively, natural products libraries or the compounds contained in the chemical libraries of the pharmaceutical companies such as Merck and Smith Kline Beecham can be screened using the assays of the present invention.

Another approach uses recombinant bacteriophage to produce large libraries. Using the "phage method" [Scott and Smith, 1990, *Science* 249:386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). Yet another approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [*14th International Congress of Biochemistry, Volume 5,* Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for such an agent.

Gene Therapy and Transgenic Vectors

The present invention further provides vectors containing one or more coding sequences operatively linked to a promoter or minimal promoter and under the control of a LCE or PACE. The tissue specificity of the PACE and LCE can ensure vector gene expression in only specifically desired tissues.

In one embodiment, a coding sequence operatively linked to a promoter or minimal promoter and under the control of PACE or LCE is introduced in vivo in a viral vector. Such vectors include an attenuated or defective DNA virus, such as but not limited to herpes simplex virus (HSV), papilloma virus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, any designated tissue or body part can be specifically targeted using a PACE of the present invention that is specific for that tissue. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828 (1989)]. Such administration can be used for experimental or diagnostic purposes. For example, a fluorescent or colored protein can be placed into a lens (e.g. when the PACE is a LCE). Alternatively, the coding sequence can encode a therapeutic protein to be used in gene therapy.

Preferably, for ex vivo administration, an appropriate immunosuppressive treatment is employed in conjunction with the viral vector, e.g., adenovirus vector, to avoid immuno-deactivation of the viral vector and transfected cells. For example, immuno suppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

In another embodiment the coding sequence can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988)]. The use of cationic lipids may promote encapsulation of negatively charged nucleic acids, and also promote fusion with negatively charged cell membranes [Felgner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

In a preferred embodiment of the present invention, a vector as described above that encodes a marker protein is inserted in the vector. That is, a specific expression vector of the present invention can be used in diagnostic procedures. An expression vector could alternatively encode a therapeutic protein.

In one embodiment, the present invention contemplates constitutive expression of the coding sequence encoding a marker protein or therapeutic protein, even if at low levels. Various therapeutic heterologous genes can be inserted in a gene therapy vector of the invention such as but not limited to adenosine deaminase (ADA) to treat severe combined immunodeficiency (SCID); marker genes or lymphokine genes into tumor infiltrating (TIL) T cells [Kasis et al., *Proc. Natl. Acad. Sci. U.S.A.* 87:473 (1990); Culver et al., *ibid.* 88:3155 (1991)]; genes for clotting factors such as Factor VIII and Factor IX for treating hemophilia [Dwarki et al. *Proc. Natl. Acad. Sci. USA*, 92:1023–1027 (19950); Thompson, *Thromb. and Haemostatis*, 66:119–122 (1991)]; and various other well known therapeutic genes such as, but not limited to, β-globin, dystrophin, insulin, erythropoietin, growth hormone, glucocerebrosidase, β-glucuronidase, α-antitrypsin, phenylalanine hydroxylase, tyrosine hydroxylase, ornithine transcarbamylase, apolipoproteins, and the like. In general, see U.S. Pat. No. 5,399,346 to Anderson et al.

Alternatively a viral vector containing a LCE of the present invention can be used to transcribe a gene product that is useful for the treatment of a corneal epithelium ailment including but not limited to superficial punctate beratitis, corneal epithelium ulcers, and herpes simplex keratitis (or kerato conjunctivitis) [see Merck Manual 16th ed., Merck Research Laboratories, Rahway, N.J. (1992)].

In another aspect, the present invention provides for regulated expression of the coding sequence (e.g. a heterologous gene) in concert with expression of other proteins under control of the PACE. Concerted control of such heterologous genes may be particularly useful in the context of treatment for proliferative disorders, such as tumors and cancers, when the heterologous gene encodes a targeting marker or immunomodulatory cytokine that enhances targeting of the tumor cell by host immune system mechanisms. Examples of such heterologous genes for immunomodulatory (or immuno-effector) molecules include, but are not limited to, interferon-α, interferon-γ, interferon-β, interferon-ω, interferon-τ, tumor necrosis factor-α, tumor necrosis factor-β, interleukin-2, interleukin-7, interleukin-12, interleukin-15, B7-1 T cell co-stimulatory molecule, B7-2 T cell co-stimulatory molecule, immune cell adhesion molecule (ICAM) -1 T cell co-stimulatory molecule, granulocyte colony stimulatory factor, granulocyte-macrophage colony stimulatory factor, and combinations thereof.

In a further embodiment, the present invention provides for co-expression of two proteins under control of the PACE or LCE. In one embodiment, these constructs are provided on separate vectors. These constructs may also be provided in a single expression vector.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

PACE, A HIGHLY CONSERVED LENS TRANSCRIPTIONAL CONTROL ELEMENT FROM THE PAX-6 GENE

Introduction

Pax-6 plays a central role in development of the lens. For example, tissue recombination experiments performed using the Small eye rat indicate that when the Sey mutation is present in presumptive lens ectoderm, formation of a lens is prevented [Fujiwara et al., *Differentiation* 57:31–38 (1994)]. Mouse small eye results from mutations in a paired-like homeobox-containing gene [Hill et al., *Nature*, 354:522–525 (1991)].

In contrast, either a wild-type or Sey optic vesicle will stimulate the formation of a lens when recombined with wild-type presumptive lens ectoderm [Fujiwara et al., *Differentiation* 57:31–38 (1994)]. In addition, experiments have been performed to generate chimeric mice by aggregating cells from wild-type and Sey 8-cell embryos. These experiments show that no Sey cells would populate the lens [Quinn et al., *Genes Dev.* 10:435–446 (1996)]. Such experiments demonstrate that in mammals, Pax-6 is required for lens development from the early stage of close contact between the optic vesicle and presumptive lens ectoderm Finally, it was recently shown that overexpressed Pax-6 can lead to the cell-autonomous formation of ectopic lenses in *Xenopus laevis* [Altmann et al., *Dev. Biol.* 185:119–123 (1997); U.S. application Ser. No. 08/846,463 filed May 1, 1997 hereby incorporated by reference in its entirety]. These lenses had many normal features including the polarization resulting from an anterior epithelium and posterior fiber cell mass [Altmann et al., *Dev. Biol.* 185:119–123 (1997)]. Such results indicate that in Xenopus ectoderm, Pax-6 expression is sufficient for lens formation. In turn, this suggests that the critical signals in lens induction are those that activate and maintain Pax-6 expression.

Materials and Methods

Cloning of the mouse Pax-6 gene. The Pax-6 gene was isolated from a mouse genomic library generated from the 129sv strain in the λFIXII vector (Stratagene) using a PCR-derived probe from the region just upstream of the P0 promoter. Three distinct λ clones were isolated, restriction mapped and found to span a 15 kilobase region that included at least 7 kilobases 5' of the P0 promoter. The 7 kilobase region upstream of the P0 promoter was subcloned and sequenced using automated techniques. Alignments to identify conserved regions of the Pax-6 gene 5' flanking sequence were performed using the Lasergene software suite.

Generation of reporter constructs. lacZ reporter constructs (FIG. 2) were generated using the plasmid phspPTlacZpA [Song et al., *Development* 122:627–635 (1996)]. phspPT-lacZpA is a reporter plasmid that contains promoter sequences (−664 to +224 relative to the start-point of transcription) from the mouse hsp68 gene and includes the translational start codon fused in-frame to a lacZ open reading frame. For the P6-3.9–3.5 construct, the PACE was amplified by PCR and subcloned upstream of the minimal hsp68 promoter. For all other reporter constructs, the hsp68 promoter was eliminated and a region of the Pax-6 gene that included the P0 promoter (to the BglII site in the 5' untranslated region) was subcloned upstream of lacZ (FIG. 2). The following oligonucleotides were used to amplify the conserved region for subcloning into the phspPTlacZpA vector using NotI and BamHI restriction sites: 5' primer: AAG GAA AAA AGC GGC CGC GGT TAC ACC AGA AGC ACC C, 3' primer; GCG GGA TCC AGT AAG AAG TTC TGC CGA AC.

Generation of transgenic mice. Regions of the Pax-6 gene were tested for activity in transcriptional regulation using a transient transgenic mouse assay [Song et al., *Development* 122:627–635 (1996)]. Reporter construct DNA was injected into mouse zygotes [Hogan et al., *Manipulating the mouse embryo: a laboratory manual* (1986)] and the embryos allowed to develop to an appropriate stage. They were then dissected from the uterus, fixed and stained for lacZ activity according to established protocols [Song et al., *Development* 122:627–635 (1996)].

Results

Figure 1:
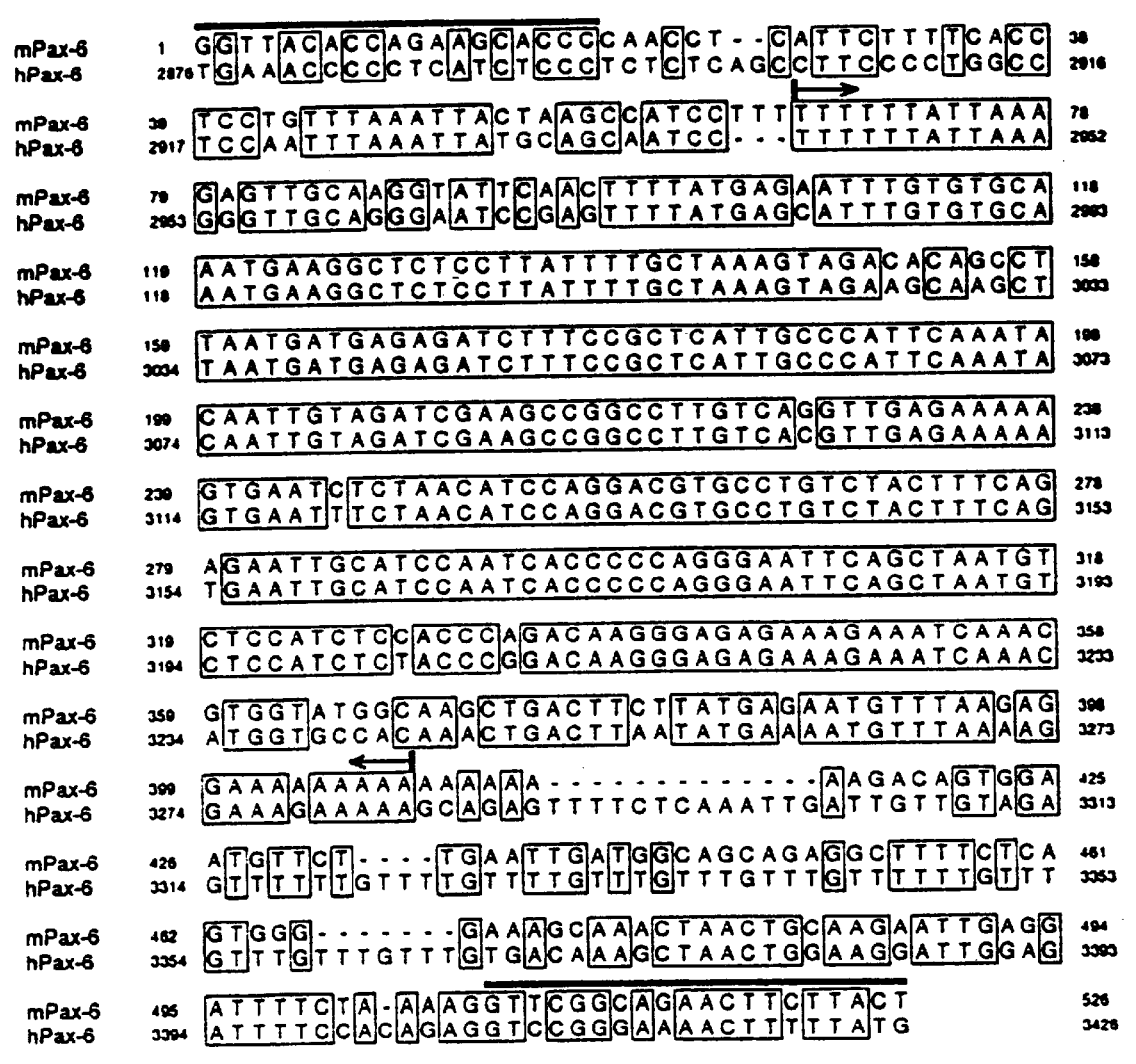

The PACE described herein was initially recognized through an alignment of the 5' flaking region from the human and mouse Pax-6 genes. This revealed a region of high identity located between 3.5 and 3.9 kilobases upstream of the P0 promoter in the mouse Pax-6 gene (FIG. 1, light gray shading). The location of the P0 promoter was identified through homology with the human sequence (accession number Z95332). The putative PACE showed only 25 mismatches in 341 nucleotides (93% conservation) but was demarcated by adjacent regions where identity was more limited (FIG. 1, dark gray shading). Based on the hypothesis that conserved regions of sequence located outside a gene might be involved in control of transcription, reporter constructs were generated to test the activity of the putative PACE.

Construct P6-5.0 contained sequences from the P0 promoter transcription start to a NotI site located approximately 5 kilobases upstream and contained the 341 basepairs region of high identity (FIG. 3). When transgenic mice were generated with this construct, X-gal staining revealed expression of lacZ in the surface ectoderm overlying the optic cup from E8.5 (12 somites) onwards (FIGS. 3A–3D). Staining in the presumptive eye region appeared initially as scattered X-gal positive cells (FIG. 3A). At E9.5, a tear-drop shaped area of ectodermal staining arose that encompassed the optic eminence and had a sharply-defined rostral boundary corresponding to the rostral boundary of the underlying optic vesicle (FIG. 3B). This region extended caudally towards the maxillary component of the first branchial arch (FIG. 3B). At E10.5, X-gal labeling became more intense in the lens pit at the center of the area of ectodermal staining but had diminished peripherally (FIG. 3B). At E12.5, intense X-gal labeling was observed in the lens together with lighter staining of an annular region of the peripheral future corneal epithelium (FIG. 3D). Labeling in a discrete region of the viscera at the level of the fore-limb buds was observed through the body wall (FIGS. 3B–3E).

To determine if any sequence 5' to the PACE had any role in the expression pattern observed with P6-5.0, construct P6-3.9 was generated. This construct contained DNA in the Pax-6 gene from the 5' boundary of the PACE to the start-point of transcription for the P0 promoter (FIG. 2). In transgenic mice, this gave an identical pattern of expression to construct P6-5.0 in components of the eye (FIG. 3E) at all stages of development. Expression in the viscera was still present though very much reduced in intensity (FIG. 3E, arrowhead).

The PACE was shown to have an eye-specific expression activity in isolation with construct P6-3.9–3.5 where the conserved region was placed adjacent to a minimal promoter from the mouse hsp68 gene (FIG. 2). When expressed in transgenic mice, this construct gave expression in the eye region with an identical pattern to that of both P6-5.0 and P6-3.9 but excluded expression from the viscera (FIG. 3F). Background expression in the neural tube typical of the activity of the hsp68 gene minimal promoter [Song et al., *Development* 122:627–635 (1996)] was observed. With all constructs containing the PACE, lacZ expression was observed at the rostral edge (FIG. 3G) and in the medial ectoderm of the first branchial arch. A construct excluding the PACE (P6-2.7; FIG. 2) gave either no expression of lacZ or ectopic expression unrelated to the pattern observed and/or anticipated for Pax-6.

Histological sections revealed that for all constructs containing the PACE, lacZ expression was restricted to eye components derived from non-neural ectoderm Expression of the reporter constructs was detectable as early as E8.5 (12 somites) with intense X-gal staining arising at E9.5 (20 somites) in the ectoderm immediately overlying the optic vesicle (FIG. 3H). At E10.5, the invaginating ectoderm of the lens pit was labeled (FIG. 3I) and at E11.0, the lens vesicle was labeled (FIG. 3J). At E12.5, the maturing lens expressed lacZ with the strongest staining appearing in the lens epithelium (FIG. 3K). From E10.5–12.5, lacZ expression was detectable in the surface ectoderm destined to become the corneal epithelium (FIGS. 3I–3K). Importantly, with all reporter constructs used to make transgenic mice, lacZ expression was excluded from both the retinal and pigmented epithelial layers of the optic cup, as well as other sites where endogenous Pax-6 expression is normally observed [Grindley et al., *Development* 121:1433–1442 (1995); Walther et al., *Development* 113:1435–1449 (1991)].

Combined, these experiments indicate that the PACE of the present invention has activity in directing transgene expression to the ectoderm that will form the lens and corneal epithelium. This region is currently delimited to 526 basepairs with a highly conserved core sequence of 341 basepairs. Interestingly, Pax-6 expression is normally detected in non-neural surface ectoderm at E8.0 [Grindley et al., *Development* 121:1433–1442 (1995)]. Since the PACE of the present invention directs expression only after E8.5, this indicates that there are additional transcriptional control elements for early ectodermal expression of Pax-6.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A nucleic acid comprising:

(a) a transcriptional control element for lens and corneal epithelium from a nucleic acid that hybridizes to a complement of SEQ ID NO:1 or SEQ ID NO:2 under stringent hybridization conditions; operably associated with (b) a nucleotide sequence that is not normally associated with the transcriptional control element, such that the transcriptional control element directs transcription of the nucleic acid not normally associated with the transcriptional control element in lens or corneal epithelium, and wherein the stringent hybridization conditions are selected for the group consisting of:

(i) 5×SSC, 0.5% SDS, and 30% formamide at 55° C.;
(ii) 5× or 6×SSC, and 40% foramide at 60° C.; and
(iii) 5× or 6×SSC and 50% foramide at 65° C.

2. The nucleic acid of claim 1 wherein the transcriptional control element contains 200 to 600 nucleotides.

3. The nucleic acid of claim 1 wherein the transcriptional control element is from a mammalian nucleic acid.

4. The nucleic acid of claim 3 wherein the transcriptional control element is from a murine nucleic acid.

5. The nucleic acid of claim 4 wherein the transcriptional control element is a Pax-6 conserved element (PACE) having the nucleotide sequence of SEQ ID NO:3.

6. The nucleic acid of claim 5 wherein the PACE comprises the nucleotide sequence of SEQ ID NO:1.

7. The nucleic acid of claim 3 wherein the transcriptional control element is from a human nucleic acid.

8. The nucleic acid of claim 7 wherein the transcriptional control element is a Pax-6 conserved element (PACE) having a nucleotide sequence of SEQ ID NO:4.

9. The nucleic acid of claim 8 wherein the PACE comprises the nucleotide sequence of SEQ ID NO:2.

10. A nucleic acid according to claim 1 wherein the nucleotide sequence that is not normally associated with the transcriptional control element encodes a polypeptide.

11. The nucleic acid of claim 10 further comprising a promoter or minimal promoter that functions in conjunction with the transcriptional control element wherein the nucleotide sequence encoding the polypeptide is operatively linked to the promoter or minimal promoter.

12. An expression vector comprising the nucleic acid of claim 11.

13. The expression vector of claim 12 wherein the polypeptide is a marker protein.

14. A method of expressing a polypeptide in a cell, which method comprises culturing a cell containing an expression vector according to claim 12 in an appropriate cell culture medium under conditions suitable for expression of the nucleotide sequence encoding the polypeptide.

15. An oligonucleotide probe that hybridizes under standard conditions with a transcriptional control element in a nucleic acid having a nucleotide sequence selected from the group consisting of SEQ ID NO:1 and SEQ ID NO:2, wherein said standard conditions comprise 5×SSC, 0.5% SDS, and 30% formamide at 55° C., and wherein the oligonucleotide has the nucleotide sequence set forth in SEQ ID NO:5 or in SEQ ID NO:6.

* * * * *